United States Patent [19]
Wang

[11] Patent Number: 5,965,818
[45] Date of Patent: Oct. 12, 1999

[54] ULTRASONIC LAMB WAVE TECHNIQUE FOR MEASUREMENT OF PIPE WALL THICKNESS AT PIPE SUPPORTS

[75] Inventor: Weicheng David Wang, Katy, Tex.

[73] Assignee: Shell Oil Company, Houston, Tex.

[21] Appl. No.: 09/007,391

[22] Filed: Jan. 15, 1998

[51] Int. Cl.[6] ................................................ G01N 29/18
[52] U.S. Cl. ................................................................ 73/598
[58] Field of Search .............................. 73/597, 598, 643, 73/637, 638

[56] References Cited

U.S. PATENT DOCUMENTS

| | | | |
|---|---|---|---|
| 4,307,616 | 12/1981 | Vasile | 73/643 |
| 5,438,872 | 8/1995 | Kobayashi et al. | 73/597 |
| 5,619,423 | 4/1997 | Scrantz | 73/638 |

Primary Examiner—John E. Chapman

[57] ABSTRACT

This invention is a new inspection technique using ultrasonic Lamb waves to measure reduction of pipe wall thickness due to localized corrosion at pipe supports. The technique uses two transducers in a pitch-catch mode to send and receive a selected Lamb wave. The wave travels along the pipe wall in the circumferential direction. The reduction of the pipe wall thickness at the pipe support changes the time-of-flight between the two transducers. By comparing time-of-flight data measured from the pipe support area and from areas adjacent to the pipe support, one can quantify the change of time-of-flight due to the pipe corrosion wall loss at the support. A mathematical model, a sizing algorithm and a PC program have been developed to quantitatively relate in time-of-flight to the minimum remaining wall thickness. With them, one can quantify the minimum remaining pipe wall thickness at a pipe support by simply measuring the change in the time-of-flight.

2 Claims, 2 Drawing Sheets

ULTRASONIC LAMB WAVE TECHNIQUE FOR MEASUREMENT OF PIPE WALL THICKNESS AT PIPE SUPPORTS

BACKGROUND OF THE INVENTION

1. Field of the Invention

The invention is directed to methods and apparatus for ultrasonically measuring pipe wall thickness at pipe supports without lifting the pipe.

2. Description of the Prior Art

Prior to this invention, qualitative inspection using Lamb waves to detect pipe corrosion wall loss at pipe supports was available. Quality NDT, Inc., having an address at P.O. Box 1145, Breaux Bridge, La. 70517, offered such an inspection service.

There was, however, no sizing technique to allow quantitative measurements of pipe wall thickness at pipe supports.

SUMMARY OF THE INVENTION

This invention is a new inspection technique using ultrasonic Lamb waves to measure reduction of pipe wall thickness due to localized corrosion at pipe supports. The technique uses two transducers in a pitch-catch mode to send and receive a selected Lamb wave. The wave travels along the pipe wall in the circumferential direction. The reduction of the pipe wall thickness at the pipe support changes the time-of-flight between the two transducers. By comparing time-of-flight data measured from the pipe support area and from an area adjacent to the pipe support, one can quantify the change of time-of-flight due to the pipe corrosion wall loss at the support. A mathematical model, a sizing algorithm and a PC program have been developed to quantitatively relate the change in time-of-flight to the minimum remaining wall thickness. With them, one can quantify the minimum remaining pipe wall thickness at a pipe support by simply measuring the change in the time-of-flight.

This is the only ultrasonic technique to the inventor's knowledge that can quantify the minimum pipe wall thickness at the pipe support without physically lifting the pipe for inspection. The quantification is absolute, i.e., it is not based on comparison with calibration defects. There is no need for calibration standards.

The principles of the technique can be used to quantify various piping defects, e.g., pits, general corrosion, corrosion at pipe supports, etc. The sizing algorithm for different defects is the same, although the mathematical model and the equations relating the defect depth to time-of-flight may need to be modified to take into account the different shapes of different defects. With modifications, this invention can be used as a general piping inspection tool.

DETAILED DESCRIPTION OF PREFERRED EMBODIMENTS

Figure 1:
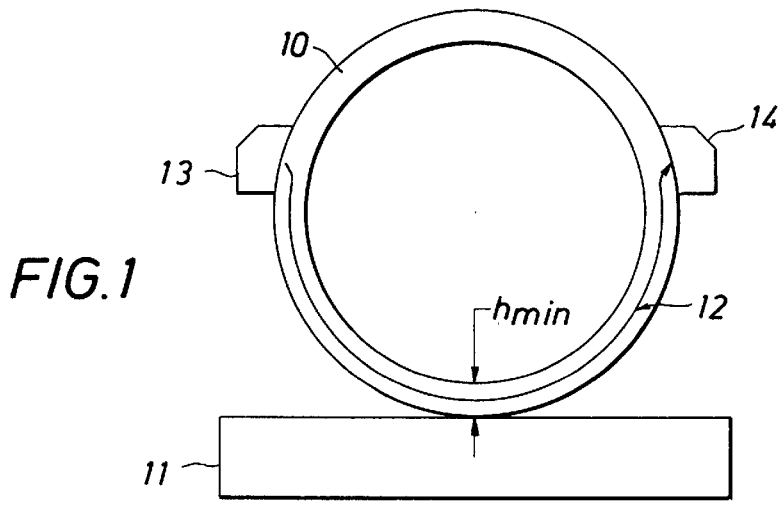
FIG. 1 is a schematic showing a method for Lamb wave inspection of a pipe at a pipe support.

As shown in FIG. 1, a pitch-catch setup is used to measure the time-of-flight of Lamb wave propagation in the circumferential direction. A pipe 10, for which it is desired to determine the minimum wall thickness, $h_{min}$, is supported by a pipe support 11. A Lamb wave 12 is "pitched" by transmitter 13 and "caught" by receiver 14. The change of material thickness affects the velocity of the wave propagation and thus the time-of-flight. By choosing a particular wave mode at a particular operating point, one can calculate the theoretical change of time-of-flight for the wave to propagate from transmitter 13 to receiver 14 due to the change of thickness. If the relationship between the thickness and the velocity is monotonic, one can uniquely determine the change of thickness from the change of time-of-flight. For example, one can choose the $S_0$ mode (i.e. the lowest order symmetric mode) Lamb wave at an operating frequency corresponding to the point where the $S_0$ mode group velocity is at its minimum. Keeping the same operating frequency, one then has a monotonic increase of the group velocity with the decrease of the material thickness. This means that any thickness reduction in the sound path will cause an increase of the Lamb wave 12 velocity and thus a decrease of the transit time for the Lamb wave 12 to propagate from the pitching transducer 13 to the catching transducer 14.

Figure 2:
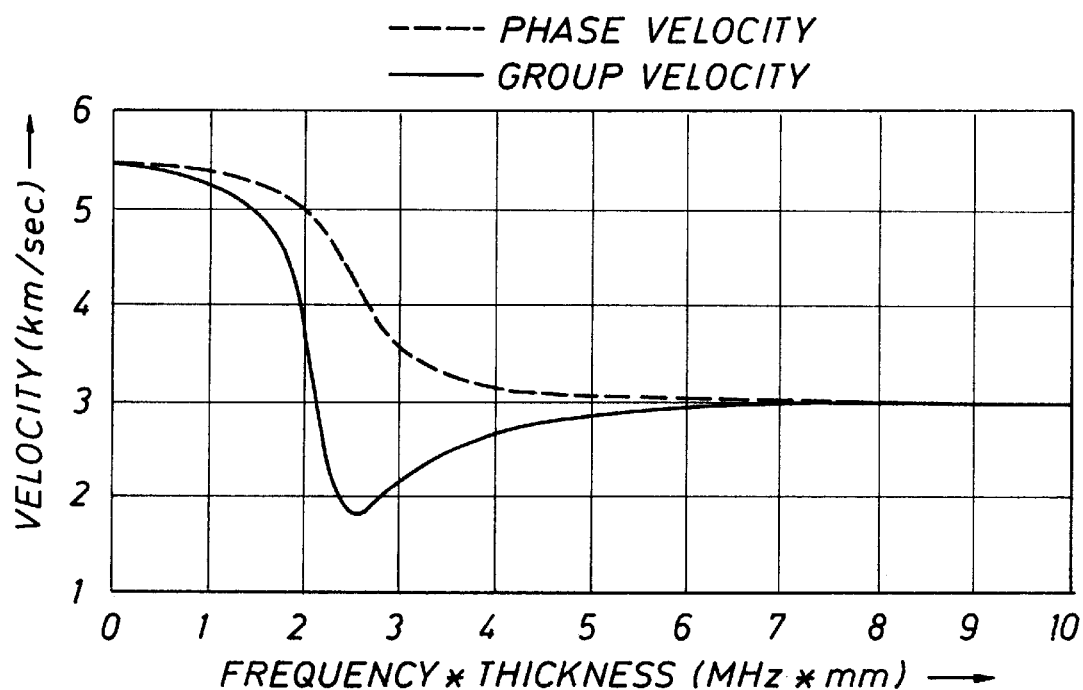
FIG. 2 shows the phase velocity and group velocity dispersion curves of $S_0$ mode Lamb wave in steel.

As an example, FIG. 2 shows the phase velocity dispersion curves and group velocity of the $S_o$ mode Lamb wave in a steel plate in vacuum having a longitudinal wave velocity equal to 5.96 km/sec, a shear wave velocity equal to 3.26 km/sec, and a density equal to 7.93 g/cm$^3$. The minimum of the group velocity occurs at f·h=2.56 MHz·mm, where f is the Lamb wave frequency and h is the material thickness. If one uses the $S_0$ mode at the frequency giving the f·h value equal to 2.56 MHz·mm for the nominal thickness, then any reduction from the nominal thickness (e.g., due to localized corrosion at pipe support) will cause a decrease in the f·h value. For example, for inspecting a pipe whose thickness is 0.375" without wall loss due to pipe-support corrosion, one can use a frequency equal to 2.56/(0.375·25.4)=0.27 MHz as the operating frequency. This gives the group velocity of the $S_o$ mode Lamb wave equal to 1.77 km/sec when there is no wall loss, i.e., it is 100% of the nominal thickness. Should there be any wall loss, the "frequency-times-thickness" value will decrease since the frequency is kept at a constant. As shown in FIG. 2, such a decrease of the f·h value will lead to an increase of the group velocity and therefore a shorter time-of-flight between the transmitting 13 and receiving 14 transducers.

There are two common methods to excite a Lamb wave at a particular point of interest. One is to use an electromagnetic acoustic transducer (EMAT) and the other is to use a piezoelectric transducer (PZT) with a wedge. With EMAT, one needs to choose a wire spacing that can generate a Lamb wave whose wavelength can satisfy the requirement for the phase velocity of the mode of interest at the operating point, as discussed in the following example. Using FIG. 2, $S_0$ mode in the steel at f·h=2.56 MHz·mm has a phase velocity equal to 4.0 km/sec. To operate on the $S_0$ mode at f·h=2.56 MHz·mm, one needs to use an EMAT wire spacing that gives the $S_0$ phase velocity equal to 4.0 km/sec at f·h=2.56 MHz·mm. For meander coils, one can use λ=2d, where λ is the wavelength and d is the wire spacing. Since Vp=f·λ, we have $$V_p = 2 \cdot f \cdot d \qquad (1)$$

For a given nominal thickness, h is known. One can determine f to satisfy f·h=2.56 MHz·mm. Using the f thus determined, one can then determine the wire spacing needed for the inspection. For example, to inspect a 0.375" thick pipe, one should use frequency f=2.56/(0.375·25.4)=0.27 MHz. The wire spacing should be 4.0/(2·0.27)=7.4 mm (0.29"). If one does not have such a wire spacing, one can adjust the frequency f so that the operating point is close to the above and the signal is at its highest amplitude level.

If one uses a piezoelectric transducer with a wedge, the phase velocity is determined as $$V_P = V_i \cdot \sin(\Theta_i) \quad (2)$$

where $V_i$ is the velocity of the incident wave in the wedge material and $\Theta_i$ is the incident angle. For a given wedge material, $V_i$ is fixed. One can adjust $\Theta_i$ to get the appropriate $V_P$ value, as in the case for EMAT. That is, the only difference between EMAT and PZT is how we generate and determine the phase velocity. For EMAT we use Equation (1), and for PZT we use Equation (2). The rest of the calculations are the same.

Figure 3:
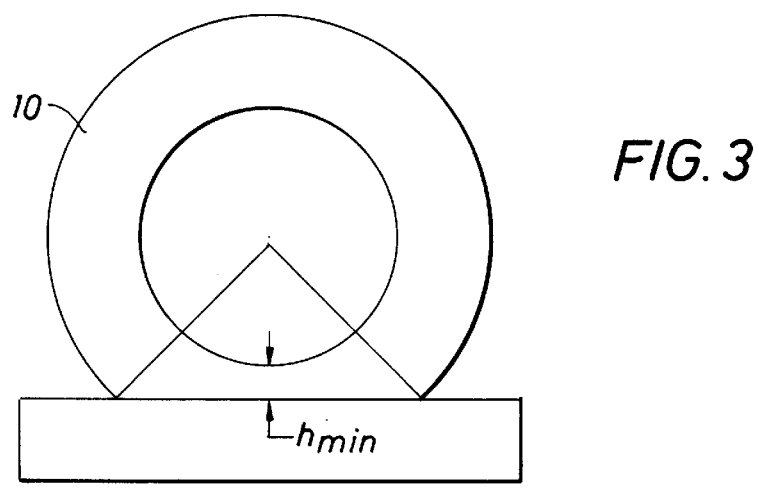
FIG. 3 shows progression of corrosion on a pipe at a pipe support.
Figure 4:
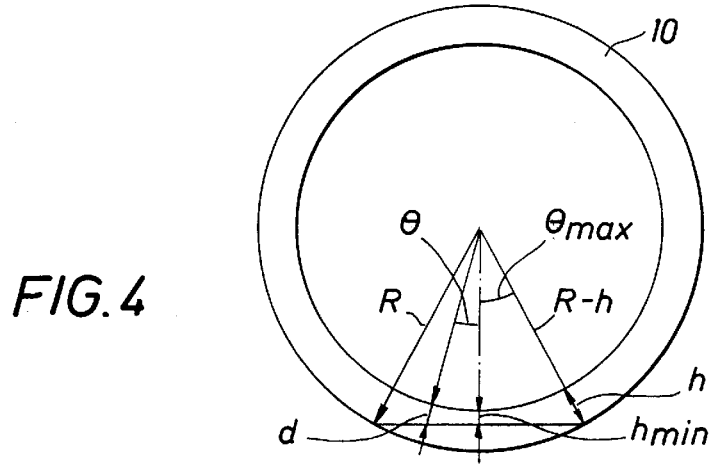
FIG. 4 shows the model for quantification of the minimum remaining wall thickness of a pipe at a pipe support.

Once a wave mode and an operating point are selected, one can quantify the minimum remaining wall thickness at a pipe support as follows:

Assume that the corrosion at the pipe support proceeds in a "tangential cut" fashion, as shown in FIG. 3. Mathematically, one can derive the following equations by using FIG. 4. As shown in FIG. 4, R is the outside radius of the pipe, i.e., R=D/2, where D is the outside diameter of the pipe; $h_{min}$ is the minimum remaining wall thickness; h is the nominal wall thickness; $\Theta_{max}$ is the maximum angle of corrosion measured from the center of the corroded area; d denotes the wall thickness within the corroded area at angle $\Theta$. Express the minimum remaining wall thickness as a fraction of the nominal wall thickness by using a new variable x, where $$x = \frac{h_{min}}{h} \quad (3)$$

From simple trigonometry, it is not difficult to find that the maximum angle of corrosion, $\Theta_{max}$, can be expressed as a function of x, h, and R:

$$\theta_{max} = \cos^{-1}\left\{1 - \frac{(1-x) \cdot h}{R}\right\} \quad (4)$$

Similarly, one can find that the wall thickness d at angle $\Theta$ can be written explicitly as a function of $\Theta$, x, h, and R:

$$d = \frac{R - h + x \cdot h}{\cos(\theta)} - R + h \quad (5)$$

Assume that the velocity of the Lamb wave at wall thickness d is $V_g(f \cdot d)$, where $V_g$ is the group velocity of the Lamb wave as a function of the product of frequency and thickness and f is the Lamb wave frequency. Similarly, the velocity of the Lamb wave at nominal wall thickness h is $V_g(f \cdot h)$. The time for the Lamb wave to propagate through the corroded area can be written as:

$$t = 2 \cdot \int_0^{\theta_{max}} \frac{R - h + \frac{d}{2}}{V_g(f \cdot d)} d\theta \quad (6)$$

while the time for the Lamb wave to propagate through an equivalent area without the pipe-support corrosion can be written as:

$$t_0 = 2 \cdot \int_0^{\theta_{max}} \frac{R - \frac{h}{2}}{V_g(f \cdot h)} d\theta \quad (7)$$

Note: $t_o$ is measured in the same manner as t except that the measurement is made at a point next to the pipe support.

The time shift due to localized corrosion at the pipe support is:

$$\Delta t = t - t_o \quad (8)$$

That is $$\Delta t = 2 \cdot \int_0^{\theta_{max}} \frac{R - h + \frac{d}{2}}{V_g(f \cdot d)} d\theta - 2 \cdot \int_0^{\theta_{max}} \frac{R - \frac{h}{2}}{V_g(f \cdot h)} d\theta \quad (9)$$

Combining Equations (4), (5) and (9), one can find that the time shift is a function of x, h, R, f. Except for x, all the parameters are easily measurable in the field and can be used as input data for calculation of Lamb wave time shift with the equations. These other parameters can be measured as follows.

The nominal thickness, h, can be measured with an ultrasonic thickness gauge. The best mode of operation is to have the thickness measured from the bottom of the pipe in an area right next to the pipe support. If the bottom can not be reached, measure the thickness from as close to the pipe support as possible.

The outside radius, R, can be calculated from the nominal outside diameter, D. R=D/2. If the nominal outside diameter is not known, calculate R by using R=C/(2·π), where C is the external circumference of the pipe, which can be measured with a tape measure.

The frequency, f, is the Lamb wave frequency used in the inspection. Preferably, this frequency is set at the value giving the f·h corresponding to the minimum group velocity of the $S_0$ mode Lamb wave, as discussed previously.

Figure 5:
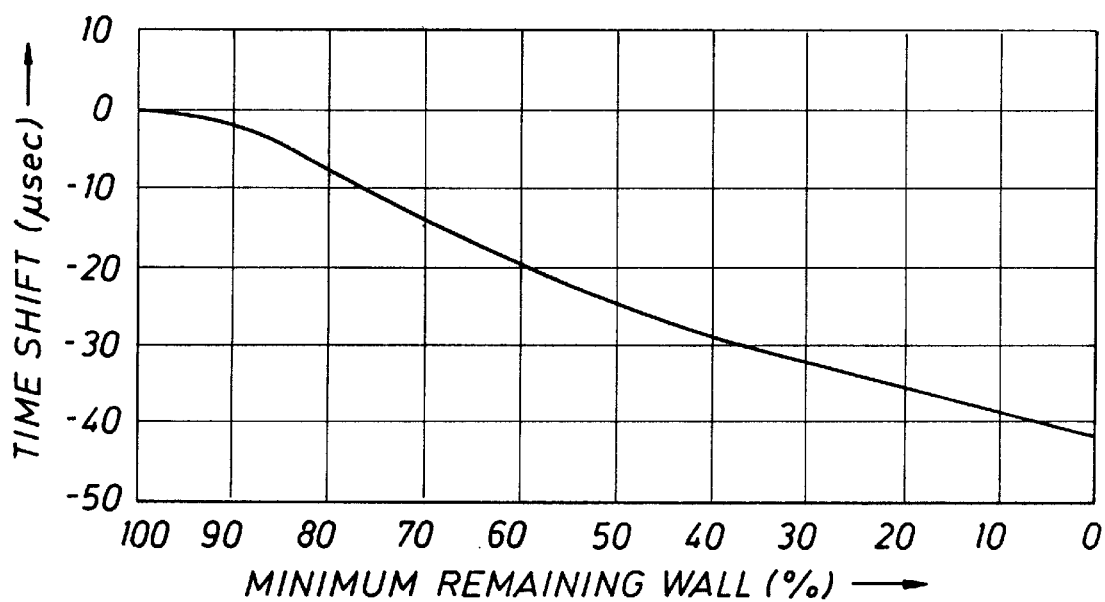
FIG. 5 shows an example of calculated time shift as a function of the minimum remaining wall thickness in percentage of the nominal wall thickness.

Using the h, R, and f values determined as above, one can then calculate $\Delta t$ as a function of x. The calculated $\Delta t$ vs x curve can then be used to determine the minimum remaining wall thickness from the measured time shift. For example, FIG. 5 shows the time shift $\Delta t$ as a function of the remaining minimum wall thickness in percentage of the nominal wall thickness by using Equations (4), (5), and (9) with h=0.437", R=7", and f=225 kHz (i.e. 0.225 MHz). This calculated curve can be used to determine the minimum remaining wall thickness of a pipe that has 0.437" nominal wall thickness and 14" outside diameter, with the $S_0$ mode Lamb wave operated at 225 kHz. As shown in the figure, for each time shift, $\Delta t$, there is a corresponding minimum remaining wall thickness.

In the best mode of operation, one should use the frequency f that gives the f·h value corresponding to the minimum group velocity of the $S_0$ Lamb wave. By choosing such a frequency, the above correlation between the time shift, Δt, and the minimum remaining wall thickness as a fraction of the nominal wall thickness, x, is always one-on-one. That is, for each time shift value, there is only one possible minimum remaining wall thickness value.

If for any reason one cannot use the frequency in the best mode of operation, it is possible to have more than one minimum remaining wall thickness values corresponding to one time shift value. In such a case, one should not use the calculated curve in the time shift range where there is more than one minimum remaining wall thickness value. The part of the curve that has a one-on-one correspondence is still valid, and can be used to determine the minimum remaining wall thickness from measured time shift.

A FORTRAN program for calculations per Equations (3), (4), (5) and (9) is included as Appendix A. This program calculates time shift as a function of the minimum remaining wall thickness. The program is for $S_o$ mode Lamb wave inspection of pipes at pipe supports. $V_g$ as a function of f·h for the $S_o$ mode in a steel plate is included.

Ultrasonic System Requirements

The combination of EMAT and Automated Ultrasonic Testing (AUT) is preferred for the above inspection. EMAT is preferred because it does not require extensive surface preparation and it can work through a thin coating. Such capabilities make scanning along pipe for a long distance possible. AUT is preferred because scanning along a pipe is desired. For Lamb wave measurements, AUT system should be able to operate in the frequency range between 100 kHz and 500 kHz. In addition, the system should allow measurements of time shift with an accuracy of at least ±0.1 μsec.

The system should be able to handle pitch-catch measurements, as shown in FIG. 1. It is also desirable to have pulse-echo capability, so that one can use pulse-echo techniques to detect such defects as pits and cracks which is not considered in the above discussion.

APPENDIX A

```
c        Filename: Pipe4.for
c        Function: Time shift vs. min. remaining wall thickhess of pipe
c                 at pipe support
c        Last Revision: July 21, 1997
c        Programmer: David Wang
c-----   Variables-------------------------------------------------
         real*8 pd, pr, ph, pf, pfl, pfi, pws, px
         real*8 tn, tps, dt, dtl, dti
         real*8 a, b, c, root
         characteer*31 name_pd, name_ph, name_pf, name_pws, name_pfl
         character*31 name_pfi, name_phase, name_root
         character*54 Col_A, Col_B, Col_C, Col_D, Col_E
         character*12 name_out
         common /emat/ thcknss, wire_sp
         external s0_err, fndrt, s0_phase, s0_group
c-----   Headers for output data columns--------------------------
         name_pd= 'Pipe outside diameter (inch): '
         name_ph= 'Norminal wall thickness (inch): '
         name_pf= 'EMAT frequency (KHz): '
         name_pws= 'EMAT wire spacing (inch): '
         name_pfl= 'Nearest mode frequency (KHz): '
         name_pfi= 'Intersect frequency (KHz): '
         name_root= 'Intersect F * H (MHZ*rnm): '
         name_phase= 'Intersect phase velocity (km/s) : '
         col_A= 'Column A: Time Shift (usec), based on EMAT freq.'
         col_B= 'Column B: Time Shift (usec), based on Lamb wave freq.'
         col_C= 'Column C: Time Shift (usec), based on intersect freq.'
         col_D= 'Column D: Minimum Remaining Wall Thickness (in)'
         col_E= 'Column E: Minimum Remaining Wall Thickness (%)'
c-----   Input data------------------------------------------------
         print *, 'Enter pipe outside diameter (inch).'
         read *, pd
         pr = pd*25.4/2
         print *, 'Enter pipe nominal wall thickness (inch).'
         read *, thcknss
         ph = thcknss*25.4
         print *, 'Enter operating frequency (kHz).'
         read *, pf
         pf = pf/1000
         print *, 'Enter wire spacing (inch).'
         read *, wire_sp
         pws = wire_sp*25.4
c-----   Output filename-------------------------------------------
         print *, 'Enter output filename.'
         read (*, 50) name_out
         format(A)
         open (10, file = name_out)
c-----   Find "true" operating point-----------------------------
         call TrueOp (ph, pf, pws, pfl)
         a = 0.1
         b = 14.0
         c = 0.00001
         root = fndrt (s0_err, a, b, c)
         pfi = root/ph
```

APPENDIX A-continued

```
c-----   Header for output file-----------------------------------
         write (10, 70) name_pd,pd
         format (A, 1x, F8.3)
         write (10, 70) name_ph,ph/25.4
         write (10, 70) name_pws,pws/25.4
         write (10, 75) name_pf,pf*1000
         write (10, 75) name_pfl,pfl*1000
         write (10, 75) name_pfi,pfi*1000
         write (10, 70) name root, root
         format (A, F7.1)
         write (10, 80) name_phase,s0_phase(root)
         format (A, 1x, F8.3, /)
         write (10, 85) col_A, Col_B, col_C, col_D, Col_E
         format (5(A, /))
         write (10, *) ' A ',' B ',' C ',' D ',
       &               ' E '
c-----   Calculate time shift (delta t) due to corrosion-----------------
c-----   Output calculated results---------------------------------------
         do 1000 px = 1.0, 0.0, -0.01
            call TimeSupp(pr, ph, pf, px, tps)
            call TimeRef(pr, ph, pf, px, tn)
            dt = tps-tn
            call TimeSupp(pr, ph, pfl, px, tps)
            call TimeRef(pr, ph, pfl, px, tn)
            dtl = tps-tn
            call TimeSupp(pr, ph, pfi, px, tps)
            call TimeRef(pr, ph, pfi, px, tn)
            dti = tps-tn
            write (10, 100) dt, dtl, dti, px*ph/25.4, px*100
100         format (F9.3, F10.3, F10.3, F8.3, F10.3)
            write (*, 100) dt, dtl, dti, px*ph/25.4, px*100
1000     continue
         close (10)
         stop
         end
ccccccccccccccccccccccccccccccccccccccccccccccccccccccccccccccccc
c                                                                c
c       Subroutines                                              c
c                                                                c
ccccccccccccccccccccccccccccccccccccccccccccccccccccccccccccccccc
c*****   Find "true" operating point*****************************
         subroutine TrueOp (ph, pf, pws, pfl)
         real*8 ph, pf, pws, pfl
         real*8 pfh, fh, delta, del_min, fh_op1, fh_op2
         open (20, file = 'check_it.txt')
         open (30, file = 'modify.txt')
         pfh = pf*ph
         del_min = 100000.00
         do 1000, fh = 0.001, 8, 0.001
            delta = (fh-pfh)**2 + (S0_phase(fh) - 2*pws*pf)**2
            if (delta .lt. del_min) then
               del min = delta
               fh_op1 = fh
            end if
            if (delta .le. del_min) then
               del_min = delta
               fh_op2 = fh
            end if
            write(20, 100) fh, S0_phase(fh), S0_group(fh)
100         format(3F12.3)
1000     continue
         write(20, 150) pfh, 2*pws*pf, S0_group(pfh)
150      format(/, 3F12.3)
         write(20, 100) fh_op1, s0_phase(fh_op1), s0_group(fh_op1)
         write(20, 100) fh_op2, s0_phase(fh_op2), s0_group(fh_op2)
         pf1 = (fh_op1 + fh_op2)/2/ph
         write (30, 200) pfh, 2*pws*pf, fh_op1, s0_phase(fh_op1),
       &                 fh_op2, s0_phase(fh_op2)
200      format(6F10.4)
         close(20)
         close (30)
         end
c*****   Calculate time in pipe at pipe support*************************
         subroutine TimeSupp(r, h, f, x, t_ps)
         real*8 r, h, f, x, t_ps
         real*8 thetamax, dtheta, theta, z, vz
         t_ps = 0.0
         thetamax = radmax(x, h, r)
         dtheta = 0.001
```

APPENDIX A-continued

```
              do 100 theta = 0.0, thetamax, dtheta
                 z= (f*r - f*h*(1 - x) )/cos(theta) - f*r + f*h
                 vz = S0_group(z)
                 t_ps = t_ps + ((r - (1 - x)*h)/cos(theta) + r - h)*dtheta/vz
100           continue
              end
c*****   Calculate time in "clean" reference******************************
              subroutine TimeRef(r, h, f, x, t_ref)
              real*8 r, h, f, x, t_ref
              t_ref = ((2*r - h)/S0_group(f*h)) * radmax(x, h, r)
              end
ccccccccccccccccccccccccccccccccccccccccccccccccccccccccccccc
c                                                            c
c     Functions                                              c
ccccccccccccccccccccccccccccccccccccccccccccccccccccccccccccc
c*****   Calculate the maximum "corrosion angle" in radian***************
              real function radmax(x, h, r)
              real*8 x, h, r
              radmax = acos (1 - (1 - x)*h/r)
              end
c     Filename: s0_err.for
c     This program calculates the difference between S0 mode phase
c     velocity and the phase velocity that EMAT can generate, i.e.
c     (2*wire_sp/thcknss)* x, where wire_sp, thcknss, and fh denote
c     EMAT wire spacing, material thickness and frequency*thickness,
c     respectively, as a function of x.
              real    function s0_err(x)
              real *8    x
              common   /emat/ thcknss, wire_sp
              external S0_phase
              s0_err = S0_phase(x) - (2*wire_sp/thcknss) * x
              end
              real function fndrt(f, x1, x2, err)
              real*8 x1, x2, err, x
              external f
              if (abs(f(x1)) .lt. err) then
                 fndrt = x1
              else
                 if (f(x1)*f(x2) .lt. 0) then
                    do while (abs(0.5*(f(x1) + f(x2))) .gt. err)
                       x= 0.5* (x1 + x2)
                       if (f(x1)*f(x) .lt. 0) then
                          x2 = x
                       else
                          x1 = x
                       end if
                    end do
                    fndrt = 0.5*(x1 + x2)
                 else
                    fndrt = 99
                 end if
              end if
              end
c     Filename: S0.for
c     This file contains two main functions:
c         S0_phase(x)
c         S0_group(x)
c     and their supporting functions for calculation of the phase and
c     group velocities of S_0 mode Lamb wave.
c
c     Programmer: W. D. Wang
c     Date: July 18, 1997
c*****   Determine phase velocity S0_phase (x), where x = F*H in MHz*mm*****
              real function S0_phase(x)
              real*8 x
              if (x .le. 2.07) S0_phase = ph_a(x)
              if (x .gt. 2.07 .and. x .le. 2.6) S0_phase = (ph_a(x) + ph_b(x))/2
              if (x .gt. 2.6 .and. x .le. 2.9) S0_phase = ph_b(x)
              if (x .gt. 2.9) S0_phase = ph_c(x)
              end
c*****   Equation ph_A (for x from 0 to 2.6)*****************************
              real function ph_a(x)
              real*8 x, a, b, c, d, e, f, g, h
              a = 5.4313019
              b = -0.99494947
              c = -5.4066428
              d = 0.33521875
              e = 1.7832773
              f = -0.040605348
```

APPENDIX A-continued

```
              g = -0.19194189
              h = 0.0010635727
              ph_a = (a + c*x + e*x**2 + g*x**3)/(1 + b*x + d*x**2 + f*x**3 + h*x**4)
              end
c*****        Equation ph_B (for x from 2.07 to 2.9)*************************
              real function ph_b(x)
              real*8 x, a, b, c, d, e, f
              a = 9.017055
              b = -0.33377479
              c = -7.1942833
              d = -0.2157153
              e = 1.4946102
              f = 0.081479093
              ph_b = (a + c*x + e*x**2)/(1 + b*x + d*x**2 + f*x**3)
              end
c*****        Equation ph_C (for x from 2.87 to 14)**************************
              real function ph_c(x)
              real*8 x, a, b, c, d, e, f, g, h, i, j, k
              a = -26.764432
              b = 3.1731512
              c = 186.55974
              d = -0.22090979
              e = -779.18481
              f = 0.0094918666
              g = 2088.2639
              h = -0.00022308578
              i = -3230.5396
              j = 2.1020006e-6
              k = 2277.2288
              ph_c = a + b*x + c/x + d*x**2 + e/x**2 + f*x**3 + g/x**3 + h*x**4 + i/x**4
              &     + j*x**5 + k/x**5
              end
c*****        Determine group velocity S0_group(x), where x = F*H in MHz*mm****
              real function S0_group(x)
              real*8 x
              if (x .lt. 2.07) S0_group = gr_a(x)
              if (x .ge. 2.07 .and. x .lt. 2.6) s0_group = (gr_a(x) + gr_b(x))/2
              if (x .ge. 2.6 .and. x .lt. 2.7) s0_group = gr_b(x)
              if (x .ge. 2.7) S0_group = gr_c(x)
              end
c*****        Equation gr_A (for x from 0 to 2.6)***************************
              real function gr_a(x)
              real*8 x, a, b, c, d, e, f, g, h, i
              a = 5.4312321
              b = -0.7684549
              c = -4.1761241
              d = 0.029047536
              e = 0.021066467
              f = 0.094991153
              g = 0.6079103
              h = -0.018744089
              i = -0.11773569
              gr_a = (a + c*x + e*x**2 + g*x**3 + i*x**4)/(1 + b*x + d*x**2 + f*x**3 + h*x**4)
              end
c*****        Equation gr_B (for x from 2.07 to 2.9)************************
              real function gr_b(x)
              real*8 x, a, b, c, d, e, f, g, h, i
              a = 57873.754
              b = -152136.76
              c = 163952.78
              d = -90146.096
              e = 23913.676
              f = -754.00387
              g = -1238.1872
              h = 299.54023
              i = -22.76067
              gr_b = a + b*x + c*x**2 + d*x**3 + e*x**4 + f*x**5 + g*x**6 + h*x**7 + i*x**8
              end
c*****        Equation gr_C (for x from 2.87 to 14)*************************
              real function gr_c(x)
              real*8 x, a, b, c, d, e, f, g, h, i, j , k
              a = -16184.396
              b = 7773.3871
              c = 23182.146
              d = -2534.1355
              e = -22549.561
              f = 536.57118
              g = 14262.646
              h = -66.619005
```

APPENDIX A-continued

```
i = 5302.6586
j = 3.6827588
k = 880.79807
gr_c = a + b*log(x) + c/log(x) + d*(log(x))**2 + e/(log(x))**2
&     + f*(log(x))**3 + g/(log(x))**3 + h*(log(x))**4 + i/(log(x))**4
&     + j*(log(x))**5 + k/(log(x))**5
end
```

What is claimed is:

1. A method for quantifying the remaining wall thickness of a pipe at a pipe support without lifting the pipe from the support and without any need for calibration samples, comprising the steps of:

a) installing a transmitting transducer and a receiving transducer on said pipe on opposite sides of said pipe support;

b) transmitting a highly dispersive and monotonic part of an $S_o$ mode Lamb wave, whose frequency multiplied by thickness values are equal to or less than the value corresponding to the group velocity minimum, into said pipe with said transmitting transducer;

c) receiving said Lamb wave with said receiving transducer;

d) measuring the time required for said transmitted Lamb wave to be received by said receiving transducer, said time being identified as the time-of-flight;

e) without changing the instrument settings, but with said transducers repositioned to points adjacent said pipe support, repeating steps a) through d) to obtain a reference time-of-flight;

f) determining the change in time-of-flight due to localized corrosion wall loss by subtracting the time-of-flight measured at the pipe support from the reference time-of-flight; and g) determining the pipe thickness at said pipe support by using said change in time-of-flight.

2. The method of claim 1 wherein a model, assuming that corrosion at the pipe support progresses in a tangential cut manner, is used to relate said time shift to the minimum remaining wall thickness.

* * * * *

UNITED STATES PATENT AND TRADEMARK OFFICE
CERTIFICATE OF CORRECTION

PATENT NO. : 5,965,818
DATED : 10/12/99
INVENTOR(S) : WANG

It is certified that error appears in the above-identified patent and that said Letters Patent is hereby corrected as shown below:

Column 1, line 58, delete "velocity" (first occurrence).

Column 2, line 29-30, delete the expressioin "shows the...of the" in its entirety and insert therefor: --shows the phase and group velocity dispersion curves of the--.

Signed and Sealed this

Tenth Day of October, 2000

Attest:

Q. TODD DICKINSON

*Attesting Officer*       Director of Patents and Trademarks